US009629533B2

(12) United States Patent
Watson et al.

(10) Patent No.: US 9,629,533 B2
(45) Date of Patent: Apr. 25, 2017

(54) MULTI-PURPOSE DENTAL INSTRUMENT

(71) Applicant: StayClear Dental Mrrror, LLC, Newark, DE (US)

(72) Inventors: Jeffrey A Watson, Fayetteville, NY (US); James L Manniso, Newark, DE (US); Mark L Manniso, Newark, DE (US); David D McClanahan, Harleysville, PA (US); James Eldon, Barto, PA (US)

(73) Assignee: STAYCLEAR DENTAL MIRROR LLC, Newark, DE (US)

( * ) Notice: Subject to any disclaimer, the term of this patent is extended or adjusted under 35 U.S.C. 154(b) by 0 days.

(21) Appl. No.: 14/947,735

(22) Filed: Nov. 20, 2015

(65) Prior Publication Data

US 2016/0143521 A1  May 26, 2016

Related U.S. Application Data

(60) Provisional application No. 62/082,268, filed on Nov. 20, 2014.

(51) Int. Cl.
| *A61B 1/253* | (2006.01) |
| *A61B 1/00* | (2006.01) |
| *A61B 1/06* | (2006.01) |
| *A61B 1/015* | (2006.01) |

(52) U.S. Cl.
CPC .......... *A61B 1/253* (2013.01); *A61B 1/00096* (2013.01); *A61B 1/00133* (2013.01); *A61B 1/00135* (2013.01); *A61B 1/00165* (2013.01); *A61B 1/015* (2013.01); *A61B 1/0684* (2013.01);

(Continued)

(58) Field of Classification Search
CPC .. A61B 1/07; A61B 1/24; A61B 1/247; A61B 1/253
See application file for complete search history.

(56) References Cited

U.S. PATENT DOCUMENTS

| 3,052,031 A | 9/1962 | Piscitelli |
| 3,082,762 A | 3/1963 | Gnehm |
| 3,638,013 A | 1/1972 | Keller |

(Continued)

FOREIGN PATENT DOCUMENTS

| WO | 2011140663 A1 | 11/2011 |
| WO | 2014140795 A1 | 9/2014 |

*Primary Examiner* — Ralph Lewis
(74) *Attorney, Agent, or Firm* — Invention To Patent Services; Alex Hobson

(57) ABSTRACT

A dental mirror instrument has a light waveguide and an airflow conduit that extend along the length of an elongated member to a mirror portion. An airflow exiting from the airflow conduit may be directed over the mirror surface to remove fluids and debris. Light from a light source is transmitted along the light waveguide and is reflected off of a back-side of a land portion through a Fresnel lens to produce a task light. A mirror may have a hydrophobic surface and this surface may have raised portions or a patterned surface that further enhances the removal of fluids or debris. The optical component of the dental instrument may be detachable to a source component and may be disposable. A flexible connector may be coupled with the source component to provide an airflow to the airflow conduit and/or electrical power to the light source.

25 Claims, 21 Drawing Sheets

(52) U.S. Cl.
CPC ....... *A61B 1/00105* (2013.01); *A61B 1/00124* (2013.01); *A61B 1/00128* (2013.01)

(56) References Cited

U.S. PATENT DOCUMENTS

| | | | |
|---|---|---|---|
| 4,279,594 A | | 7/1981 | Rigutto |
| 4,807,599 A | * | 2/1989 | Robinson ................. A61B 1/07 433/29 |
| 4,925,391 A | | 5/1990 | Berlin et al. |
| 4,931,015 A | | 6/1990 | Amadei |
| 4,993,945 A | | 2/1991 | Demand et al. |
| 5,139,420 A | | 8/1992 | Walker |
| 5,139,421 A | | 8/1992 | Verderber |
| 5,457,611 A | | 10/1995 | Verderber |
| 5,951,284 A | | 9/1999 | Lake |
| 6,106,159 A | | 8/2000 | Bushroe et al. |
| 6,443,729 B1 | | 9/2002 | Watson |
| 6,544,036 B1 | * | 4/2003 | Brattesani ............ A61B 1/0607 433/29 |
| 6,575,744 B1 | | 6/2003 | Oshida |
| 6,702,577 B2 | | 3/2004 | Wong |
| 6,867,864 B2 | | 3/2005 | Overbeck et al. |
| 8,088,066 B2 | * | 1/2012 | Grey ...................... A61B 17/02 600/212 |
| 8,172,571 B2 | * | 5/2012 | Watson ................. A61B 1/253 433/31 |
| 8,684,577 B2 | * | 4/2014 | Vayser ................. A61B 1/0623 362/333 |
| 2003/0207229 A1 | * | 11/2003 | Wong ................. A61B 1/0669 433/31 |
| 2010/0190129 A1 | | 7/2010 | Paz |

* cited by examiner

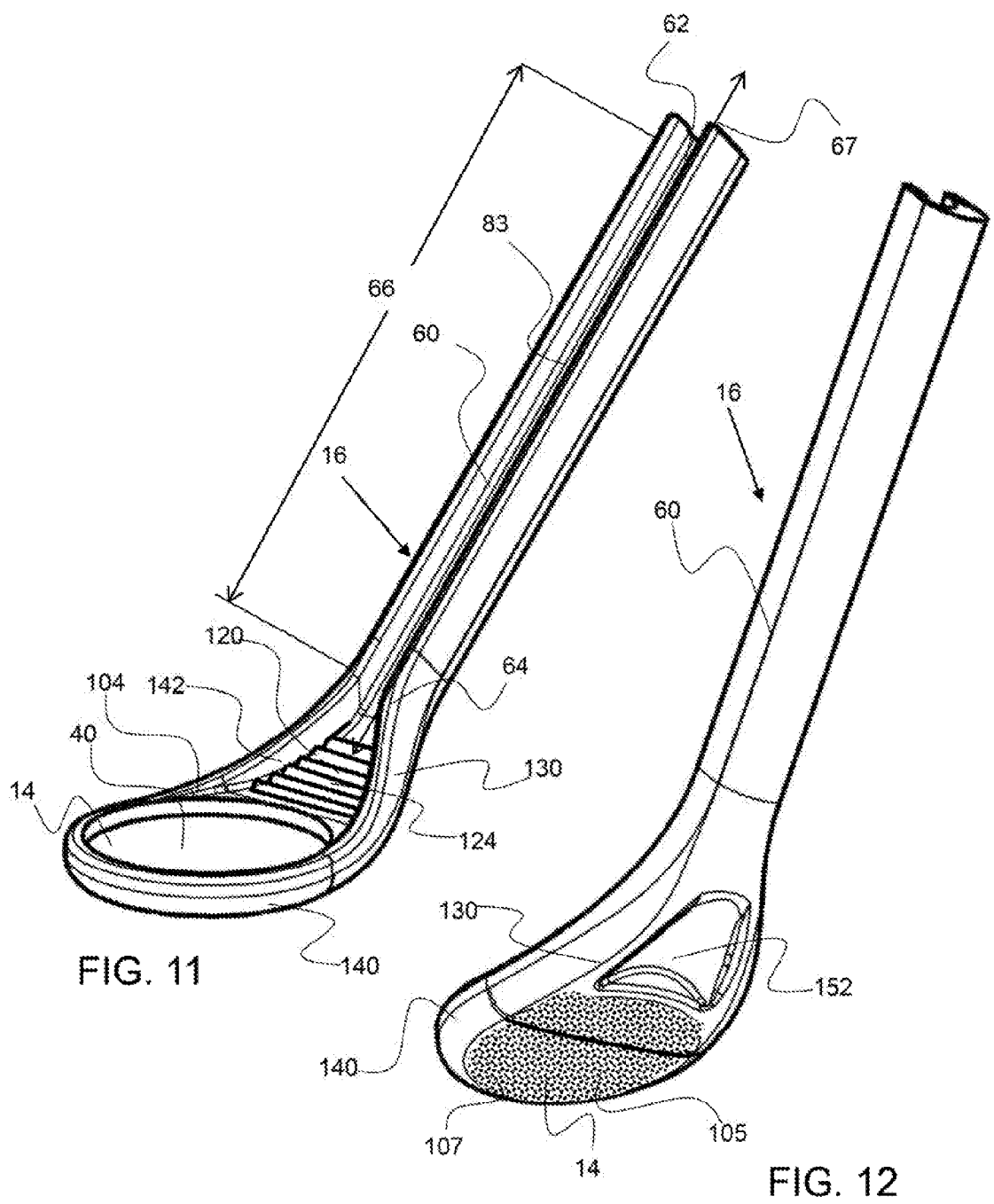

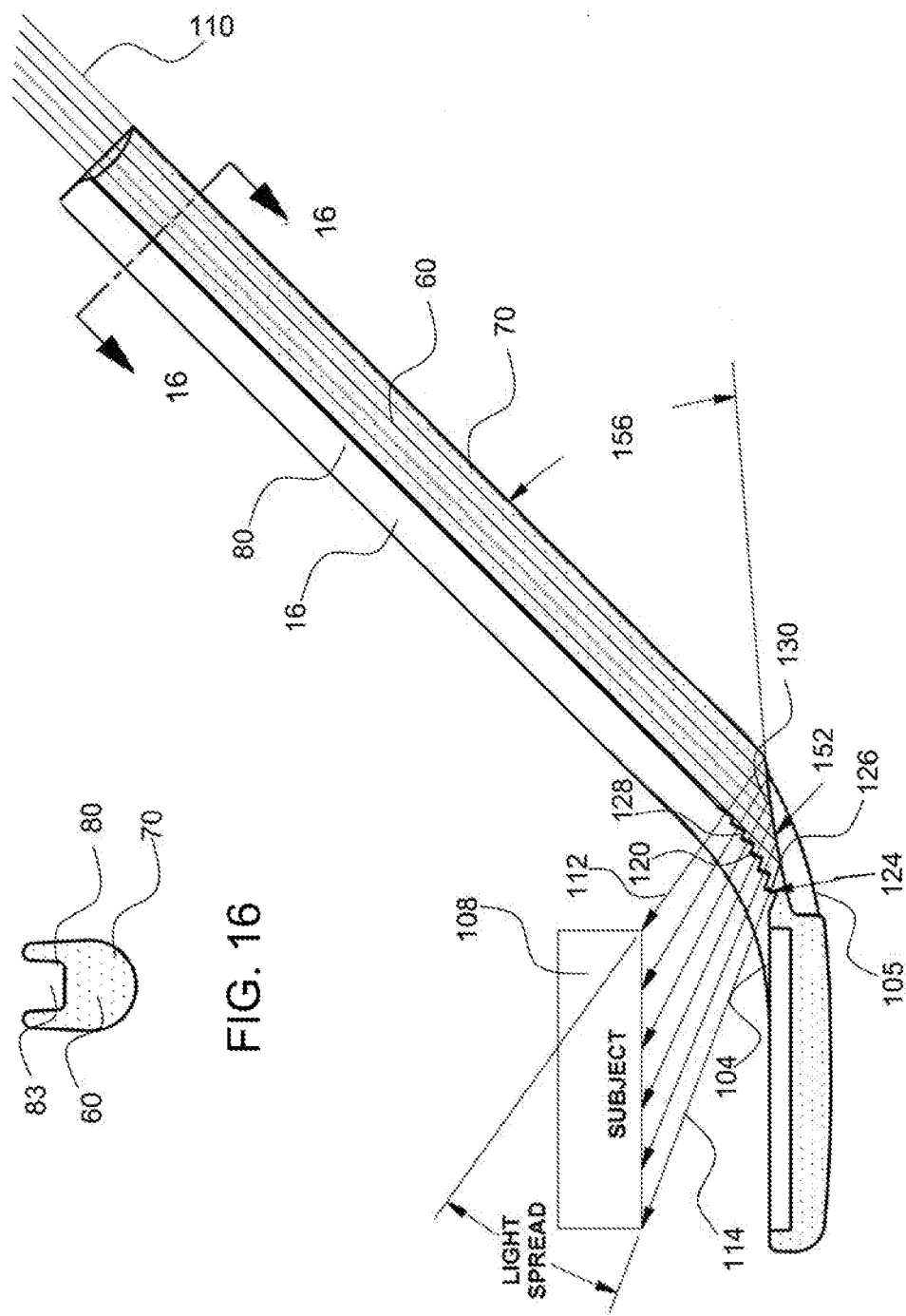

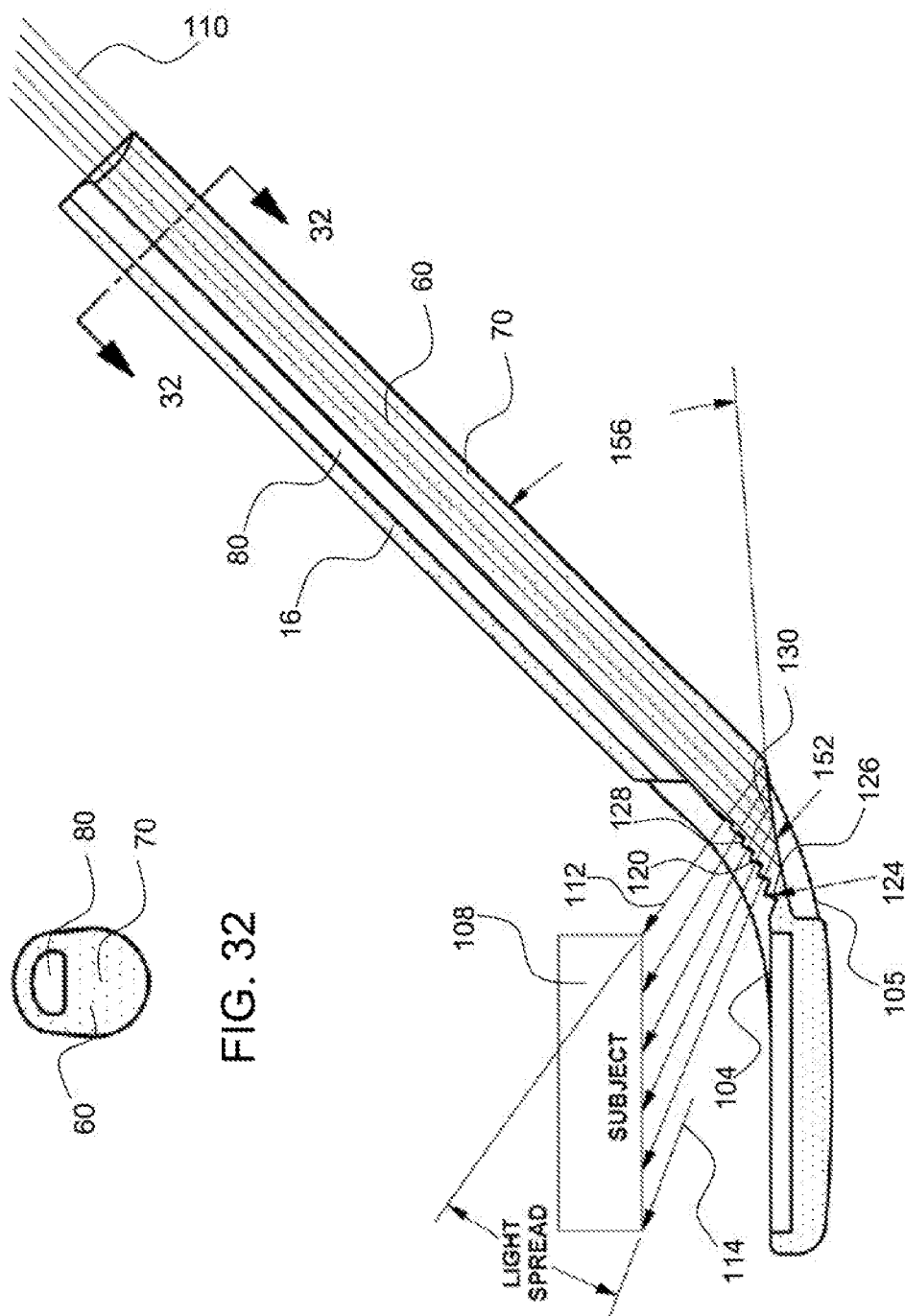

MULTI-PURPOSE DENTAL INSTRUMENT

CROSS REFERENCE TO RELATED APPLICATIONS

This application claims the benefit of U.S. provisional patent application No. 62/082,268, filed on Nov. 20, 2014 and entitled, Multi-Purpose Dental Instrument; the entirety of which is incorporated herein by reference.

BACKGROUND OF THE INVENTION

Field of the Invention

The present invention relates to a dental mirror instrument configured to illuminate the mirror surface and provide a flow of air across the mirror surface to remove liquids and debris and prevent fogging.

Background

Dental mirrors are routinely used by dentist and clinicians to view various parts of a patient's mouth and/or oropharynx. Dental mirrors are used for examination, diagnosis, procedural purposes, dental hygiene and other medical and veterinarian disciplines, such as otolaryngology (earn nose and throat ENT). The mouth is a difficult environment, as there are any number of fluids that can come into contact with the mirror surface including, saliva, mucin, rinsing water, blood, cleaning solutions and pastes as well as debris from conducting dental procedures. A mirror surface may become coated with one or more of these fluids and/or debris thereby obstructing a clear view. In addition, without proper lighting, many parts of the mouth are difficult to see even with the aid or a mirror. Lighting projected into the mouth has limited effectiveness, as many areas within the mouth are obstructed from illumination. With the aid of an illuminated mirror, light can be easily reflected into obstructed areas.

As described in U.S. Pat. No. 8,172,571, to Dr. Watson, dental mirrors have traditionally not been designed for ergonomics. In addition, traditional dental mirrors are not ergonomic. Ergonomics refers to the ease and precision with which instruments can be positioned for control, direction, duration and distance of applied force. When dental clinicians changed posture in the late 1960s from a standing position to a sitting position, the same dental mirrors remained. The angle of the traditional dental mirror surface to the mirror handle is set at approximately thirty-eight degrees. This angle supplies reflected vision for an operator who stands slightly behind, completely behind, or beside a seated patient. However, the standard thirty-eight degree angle is not designed for clinicians sitting in relation to a patient. The entirety of U.S. Pat. No. 8,172,571 is hereby incorporated by reference.

There exists a need for an illuminated dental mirror instrument that can effectively remove liquids and debris from the mirror surface and prevent fogging to allow an operator to view reflections within the mirror effectively.

SUMMARY OF THE INVENTION

The invention is directed to a dental instrument and, in an exemplary embodiment, a dental mirror instrument that is configured to illuminate the mirror surface and provide a flow of air across the surface to remove liquids and prevent fogging. The mirror surface may comprise a hydrophobic coating to facility the removal of fluids and debris. An exemplary dental mirror instrument comprises an optical component having an elongated member, a land portion and a mirror portion. A light waveguide and an airflow conduit extend along the elongated member from the engagement end to the mirror end. A Fresnel lens may be configured on a front side of the land portion and be configured to emit a task light on to a subject, such as a tooth. The land portion may also comprise an internal convex mirror surface that is configured to reflect light transmitted down the light waveguide. The internal convex mirror surface reflects the light to produce a spread of reflected light that is emitted through the Fresnel lens. The mirror portion may comprise a mirror and a light emitting perimeter portion that extends radially around a portion of the mirror to produce a radiant light.

The optical component may comprise an optical sheath that extends down over the elongated member. The optical sheath may produce a flow conduit out of a channel in the elongated member.

The optical component may receive a flow of air from a source component that is attached to the engagement end. The source component may receive a flow of air from a flexible connector that is coupled with an auxiliary pack, a docking station or a fixed source, such as a wall connector. An auxiliary pack or docking station may comprise a pump for producing a flow of air, or may be coupled by a separate flexible connector to a fixed source. The airflow conduit may be formed from an airflow channel in the optical component and an optical sheath configured thereover. An optical component may comprise a continuous conduit through the elongated member in another embodiment. The flow of air may be heated by the optical component and light waveguide as it passes along the airflow conduit in the elongated member. This heated flow of air may be more effective at removing fog from the mirror.

An optical component may receive light from a light source that is configured in a source component. A Light Emitting Diode (LED), may be configured in the source component and provide light to the light waveguide. The engagement end of the light waveguide may be concave in shape to more effectively receive and transmit the received light from the light source and to reduce heat. In an alternative embodiment, the engagement end of the light waveguide is flat or convex in shape. A light source may receive electric power from an electrical cable that extends through a flexible connector or from a battery configured, in the dental instrument, an auxiliary pack, or docking station.

A Fresnel lens may be positioned on the front-side of the land portion and be configured to disperse reflected light from the back-side of the land portion to a subject. A Fresnel lens may comprise a plurality of ridges that extend across the front-side of the land portion in a direction substantially perpendicular to the length axis of the elongated member. A ridge comprises a step and a rise, wherein the rise is a planar surface that extends substantially perpendicularly to a reflected light from the back-side of the land portion, and the step is a planar surface that extends substantially parallel to a reflected light from the back-side of the land portion. The ridges may be configured in a convex shape along the front-side of the land portion from the elongated member to the mirror portion to provide an airflow contour to direct and guide the flow of air from the airflow conduit across the mirror surface.

A land portion may comprise an internally convex, shaped mirror surface configured along a portion of the back-side of the land portion to reflect internal light toward the front-side of the land portion and through the Fresnel lens. The internally convex shaped mirror surface is configured to spread the reflected light radially between the elongated member and the mirror portion and also radially in a direction across the width of the optical component, perpendicular to the length axis of the elongated member. In a preferred embodiment, the optical component comprises a Fresnel lens and a internally convex shaped mirror surface.

A land portion may comprise a pair of ribs that extend around either side of the Fresnel lens from the elongated member to the mirror perimeter portion. The ribs may couple the light waveguide with the mirror perimeter portion and transmit light to the mirror perimeter portion. Light traveling around the mirror perimeter portion will be emitted from the surface and create a radiant light that can be used to illuminate an oral cavity. The task light, or light reflected from the back-side of the land portion through the Fresnel lens in configured to be directed onto a subject, or tooth, which is reflected in the mirror. These two distinct sources of light being emitted by the optical component provide very effective illumination of the oral cavity for a wide variety of procedures.

A dental mirror instrument, as described herein, may comprise a light source and/or an airflow source. A light source and/or airflow source may be configured in a handle or a source component. A light source may be a light emitting diode (LED) that is configured proximal to the source end of the light waveguide and may contact the light waveguide. An airflow source may comprise a fan that is configured in the handle or a source component. A light source and/or airflow source may be powered by one or more batteries that are configured in a handle or a source component. In an exemplary embodiment, a handle comprises a battery pack that powers a fan or pump, such as a mini-pump configured within the handle. In another embodiment, a battery pack powers the light source. In still another embodiment, an auxiliary pack is tethered to the dental mirror and comprises a battery and/or an airflow device such as a fan or pump. A dental instrument may be completely untethered in one embodiment and have a battery pack that powers both a fan, or other air-moving device, and a light source. An untethered portable dental instrument, as described herein, may be ideal for hospitals and nursing home use as the instrument may be required to be carried from one room to another. Patients may be examined with the aid of the portable dental mirror instrument in the comfort of their own beds, for example.

In another embodiment, an airflow source is a remote airflow source and a hose is coupled with the dental instrument to deliver a flow of air from the remote source through the hose to the dental instrument. A remote airflow source may be a fixed source from a dental office or procedure room. A compressor may supply compressed air to one or more procedure rooms within a dental or other medical facility. The air supplied to the procedure rooms may be cleaned and filtered to meet any regulations for oral procedures. A user of the dental instrument may attach a hose to an outlet in the wall of the procedure room to provide a flow of air to the dental mirror instrument. Likewise, power for the airflow source and/or light source may be provided by an electrical supply cable that is coupled with the dental instrument. A conduit providing airflow may also be coupled with the optical component or handle. A quick disconnect may be configured for detachably attaching an airflow conduit and/or power supply to the dental mirror instrument, as described herein.

A dental instrument, as described herein, may be a one-piece unit wherein the optical component and mirror portions are constructed from a single material, such as through molding. In another embodiment, the mirror portion is detachable from the optical component. A mirror portion may comprise a detachable mirror, whereby a disposable mirror can be replaced between each patient. A mirror portion may comprise a recess for receiving and retaining a detachable or disposable mirror. In another embodiment, a mirror portion is detachable from the elongated member and an auxiliary light waveguide may be attached to the elongated member, thereby providing an extension to the light waveguide for transillumination of portions of the mouth and particularly a tooth. A dental instrument, as described herein, may be used for examination, diagnosis, procedural purposes, dental hygiene and other medical and veterinarian disciplines, such as otolaryngology (earn nose and throat ENT). A dental instrument, as described herein may also be used for transillumination of the mouth and particularly a tooth. An auxiliary light waveguide may be inserted into and attached to the elongated member, thereby providing an extension to the light waveguide for transillumination of portions of the mouth and particularly a tooth. A camera may be implemented for capturing transilluminated images for future referral and examination. For example, a mini-camera may be configured to attached to the handle portion of a dental instrument for capturing transilluminated images of a tooth. In another embodiment, a camera mounted on a user's head, such as on a heads-up device, is configured on a user's eyewear and is configured to take pictures of what the user is viewing, such as a transilluminated tooth. A heads-up device may be controlled at least in part by verbal commands and a user may simply instruct the head-up camera to take photo as desired. A heads-up device may comprise a small video display in the field of view of the viewer, such as within a portion of the eyewear and a user may provide a verbal command to the camera to zoom, change focus, or change position before instructing the camera to capture a photo of a desired image.

In still another embodiment, a dental instrument, as described herein, is configured for use as a diagnostic tool using the flow of air to check for sensitive areas within the mouth, including sensitive areas on a tooth. A user may utilize the flow of air coming from the dental instrument with the mirror portion removed and in some cases an auxiliary air guide attached to direct the airflow. A user may direct the flow of air to an area of the mouth and request that the patient alert the user when they feel sensitivity from the flow of air. A sensitive area may indicate exposed nerves, or a cavity, for example.

An exemplary optical component, mirror portion, mirror and elongated member may be cleaned or sterilized separately or coupled together. A dental mirror instrument or the optical component of a dental mirror instrument may configured to be autoclaved, being made out of materials that can withstand the autoclave environment. In addition, a sleeve or protective cover may extend from a handle down over a portion of the optical component, such as the elongated member, to prevent any bodily fluids from entering into the airflow conduit. In still another embodiment, the optical component is configured to be disposable.

The mirror surface may comprise a hydrophobic coating to facility the removal of fluids and debris. In an exemplary embodiment, a hydrophobic release coated mirror includes a surface having a surface energy of less than about 20 dynes/cm and may be an oleophobic surface. A hydrophobic release surface may have a topology that enhances the removal of liquids and may be configured to cause liquids to roll-off with the force of the airflow across the mirror surface.

In an exemplary embodiment, the mirror comprises a hydrophobic release surface or coating. A mirror body may comprise any suitable material including glass or plastic and a minor coating or layer may be configured on the mirror body. A hydrophobic release surface may comprise a coating that is substantially continuous over the mirror surface or discontinuous. Discrete areas of the mirror surface may be coated with a hydrophobic release material. A hydrophobic release surface may comprise a continuous film layer that is attached to the mirror. In addition, a hydrophobic release surface may be formed by molding or stamping. For example, a mirror may be configured with a low surface energy material that is stamped or molded to produce a topographical surface having surface features as described herein. A hydrophobic release surface may be chemically etched, deposited through plasma spraying, ion beams, plasma ablation, thermally embossing, and laser treatment, for example. A hydrophobic release surface may be substantially transparent to provide a clear view of the mirror. In an exemplary embodiment, a hydrophobic release surface comprises a topology that enhances the removal of liquids and debris, A hydrophobic release surface having a topology may have increased liquid roll-off properties. For example, a hydrophobic release surface may have a topology with raised portions and depressed portions. The scale of the raised and depressed regions of a hydrophobic release surface may be configured specifically to enhance liquid roll-off and may be on the order of millimeters, micrometers, or nanometers. In an exemplary embodiment, topographical features on the mirror surface are on the micrometer to nanometer scale and are essentially transparent. The contact angle of a liquid on a hydrophobic release surface having a topology of raised and/or depressed regions may be greatly increased and the reduced contact of the liquid with the surface improves liquid roll-off. A hydrophobic release surface may comprise a patterned surface including, but not limited to, dots or discrete raised regions or portions, domes shape prominences, striations, channels and the like. In an exemplary embodiment, a hydrophobic release surface is etched, molded or otherwise formed into the surface of the mirror and therefore does not require a separate coating of material. A molded or etched surface may be more durable than a coating as it will not be susceptible to washing off.

A hydrophobic release surface may comprise a material that has low surface energy such as a fluoropolymer including, but not limited to, polytetrafluoroethylene (PTFE), fluorinated ethylene propylene (FEP), hexafluoropropylene (HFP), amorphous fluoroplastic such as Teflon AF that in an exemplary embodiment comprises Dioxole/TFE copolymer, available from E.I. du Pont de Nemours Inc., and the like. A hydrophobic release coating may have a critical surface energy of about 20 dynes/cm or less, about 18 dynes/cm or less, about 15 dynes/cm or less, about 10 dynes/cm or less, and any range between and including the surface energy values provided. In an exemplary embodiment, the hydrophobic release coating is essentially oleophobic, whereby the release coating prevents oils from wetting and spreading on the surface of the mirror. The hydrophobic release coating may be made out of materials that are non-toxic as they will be exposed to a person's bodily fluids when conducting procedures within the mouth.

In an exemplary embodiment, a hydrophobic release surface is configured with a topology that is oriented to further improve liquid removal as a function of the direction of a flow of air across the mirror surface. A flow of air from the apertures in the mirror end of the elongated member may be directed by baffles to flow substantially parallel with the mirror surface; from the back portion to the front portion of the mirror. The back portion of the mirror portion may not comprise a mirror and may direct provide a location where the light impinges, thereby eliminating any light hot-spots. A light hot-spot is an area on a mirror that is very bright or produces a glare from a direct reflection of a light hitting the surface. A patterned hydrophobic release surface may be oriented with respect to this flow of air direction to enhance liquid roll-off. For example, a hydrophobic release surface may comprise channels and these channels may be aligned with the direction of airflow, aligned perpendicular to the flow of air or aligned at some offset angle to the flow of air. In addition, a flow of air that is parallel with the mirror surface may promote liquid removal across the entire surface of the mirror.

A light waveguide may have any suitable index of refraction including, but not limited to, about 1.2 or more, about 1.3 or more, about 1.5 or more and any range between and including the values provided. A light waveguide may be a one-piece unit with the optical component such as through molding. A light waveguide may comprise or consist essentially of acrylic, polycarbonate, glass and the like. A light waveguide may have any suitable shape and, in an exemplary embodiment, is rod shaped and extends along the back-side of the elongated member. In an exemplary embodiment, the optical component including the elongated member, the land portion and the mirror portion are a one-piece unit, such as through injection molding and may be molded out of a plastic that is not suitable for conventional sterilization methods. Conventional sterilization methods including, steam, chemical methods including application of alcohols or soaking in alcohol, or autoclaving may render the optical not useable. High heat sterilization methods such as steam sterilization may cause the optical component to at least partially melt of soften and therefore warp out of shape. Chemical sterilization may leave the mirror hazy and not suitable for subsequent procedures.

The airflow conduit extends along the length of the elongated member and terminates at the mirror end in one or more apertures. These apertures may be configured to direct the flow of air in a parallel direction over the mirror surface. In another embodiment, a baffle is configured to direct the air exiting the one or more apertures across the plane of the mirror in a parallel direction. The airflow conduit cross-sectional area may be reduced at the mirror end to increase the velocity of the airflow from the one or more apertures.

In one embodiment, the mirror portion of the optical component is detachable from the elongated member thereby allowing the optical component to be used for illumination including trans-illumination. The light emitted from the mirror end of the elongated member may be used to illuminate the mouth or to provide illumination through a tooth to identify variations in density of a tooth. An auxiliary light waveguide may be attached to the elongated mirror and abut the emitting end of the light waveguide configured within the elongated member. An auxiliary light waveguide may be straight or curved and may have any suitable length.

Where there are discrepancies between this application and the provisional patent application No. 62/082,268, incorporated herein by reference, this application shall dominate.

As used herein, the term substantially perpendicular means a surface is configured about 90 degrees, 75 degrees to 105 degrees, to another surface or a light ray. Preferably, a substantially perpendicular surface is within about 80 to 100 degrees from another surface or light ray and more preferably within 85 to 95 degrees.

As used herein, the term substantially parallel means a surface is configured about 0 degrees, 15 degrees to −15 degrees, to another surface or a light ray. Preferably, a substantially perpendicular surface is within about 10 to −10 degrees from another surface or light ray and more preferably within 5 to −5 degrees.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of his specification, illustrate embodiments of the invention, and together with the description serve to explain the principles of the invention.

DETAILED DESCRIPTION OF THE ILLUSTRATED EMBODIMENTS

Figure 1:
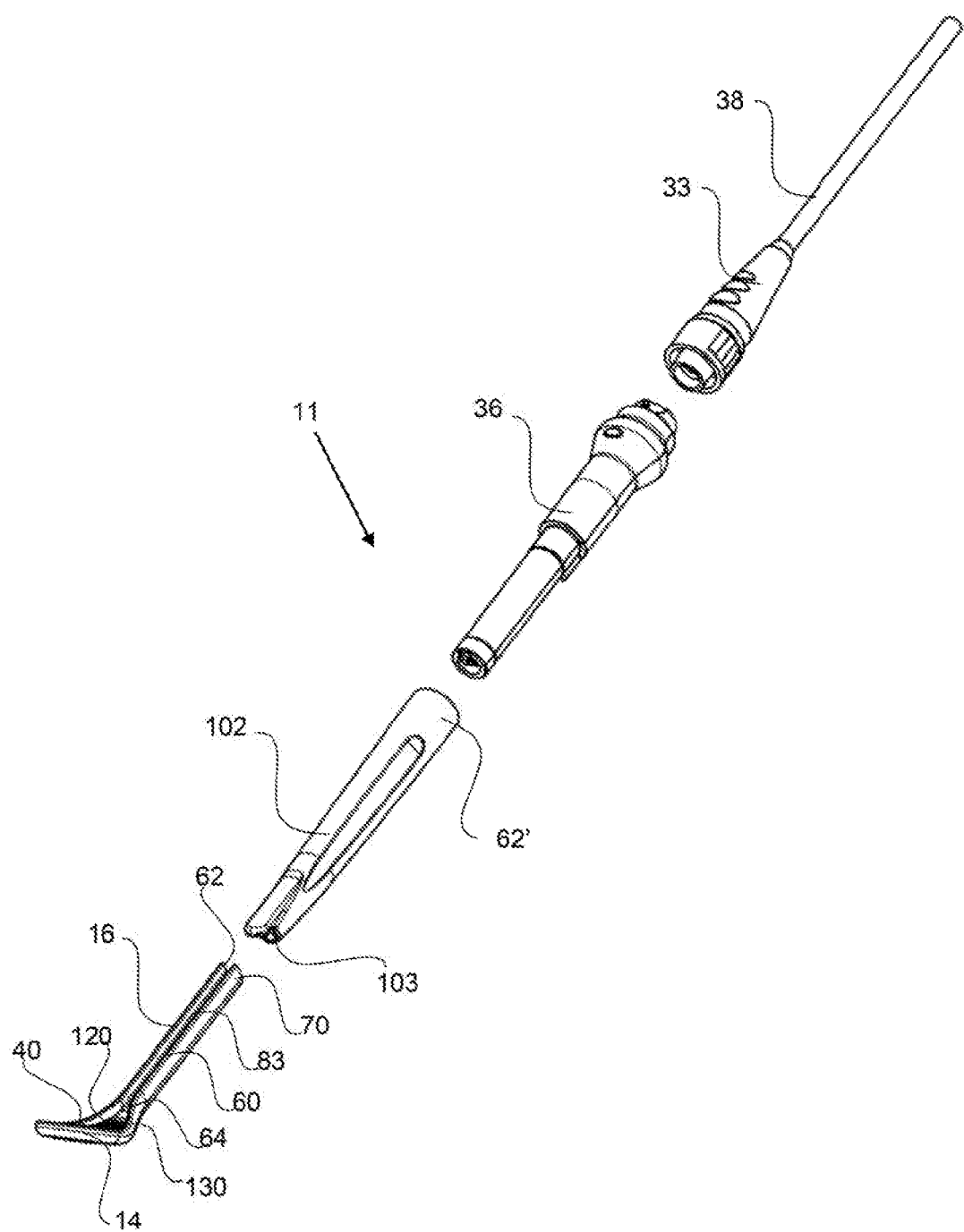

FIG. 1 shows an exploded perspective view of an exemplary dental instrument having an optical component, a sheath, a source component and a flexible connector.

Figure 2:
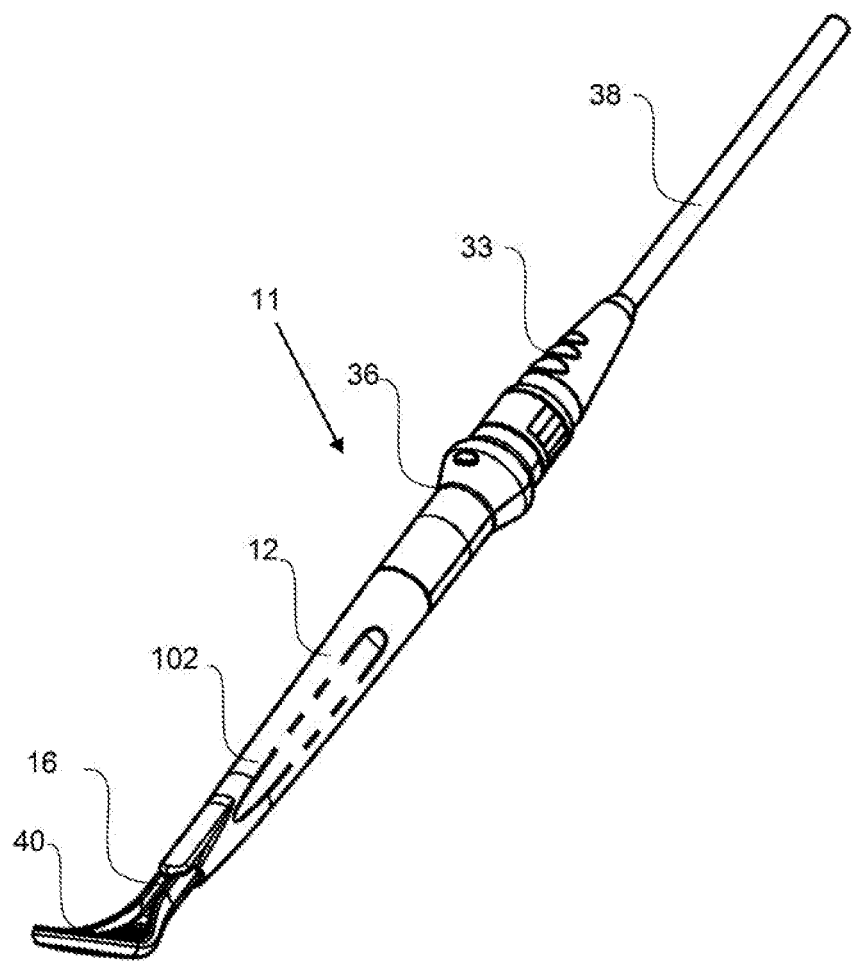

FIG. 2 shows a perspective view of the exemplary dental instrument shown in FIG. 1 with the all of the detachable components attached.

Figure 3:
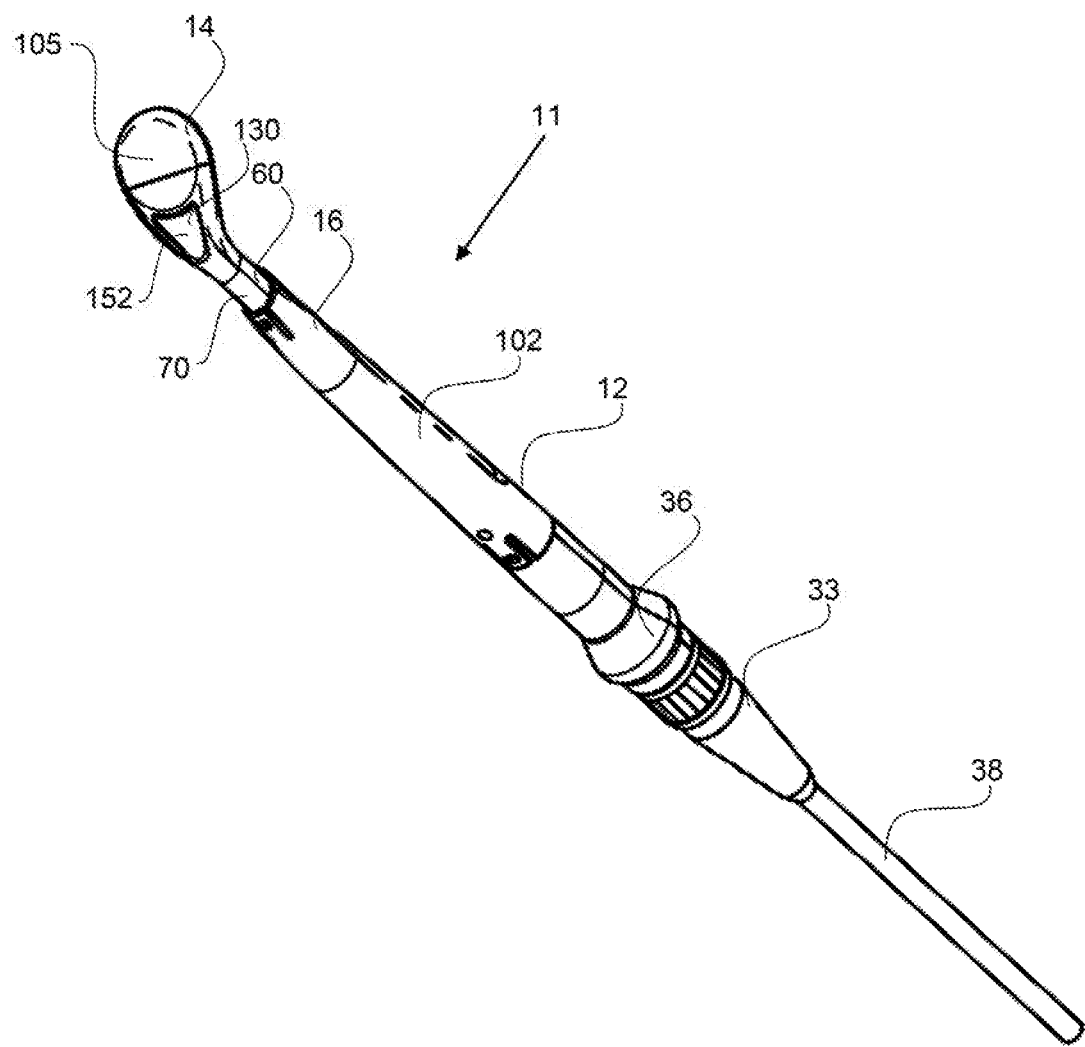

FIG. 3 shows a back-side perspective view of the exemplary dental mirror instrument shown in FIG. 2.

Figure 4:
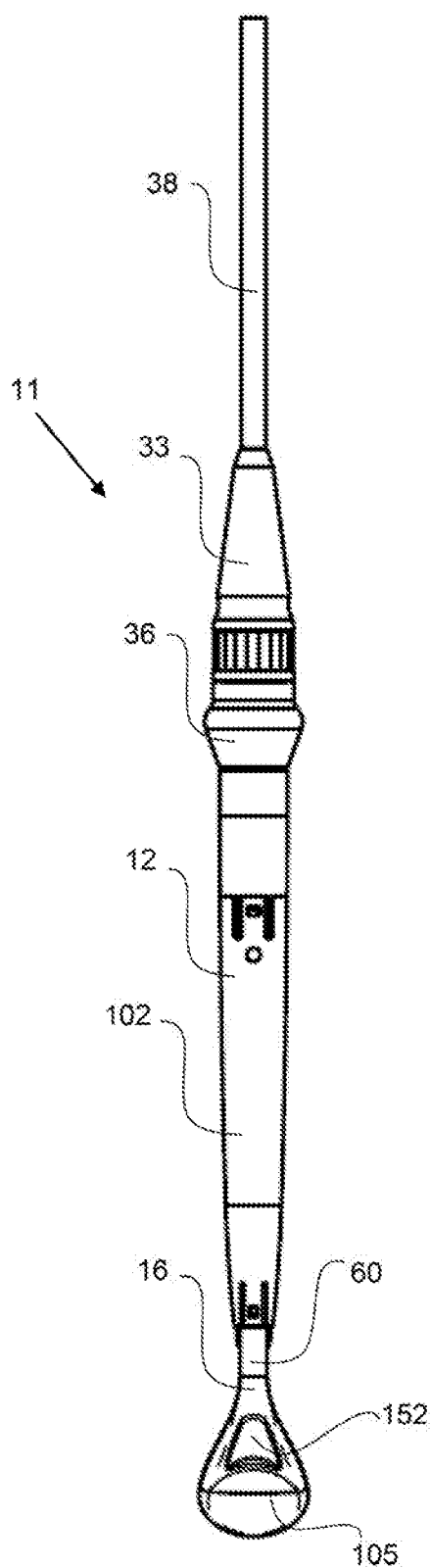

FIG. 4 shows a back view of the exemplary dental instrument shown in FIG. 2.

Figure 5:
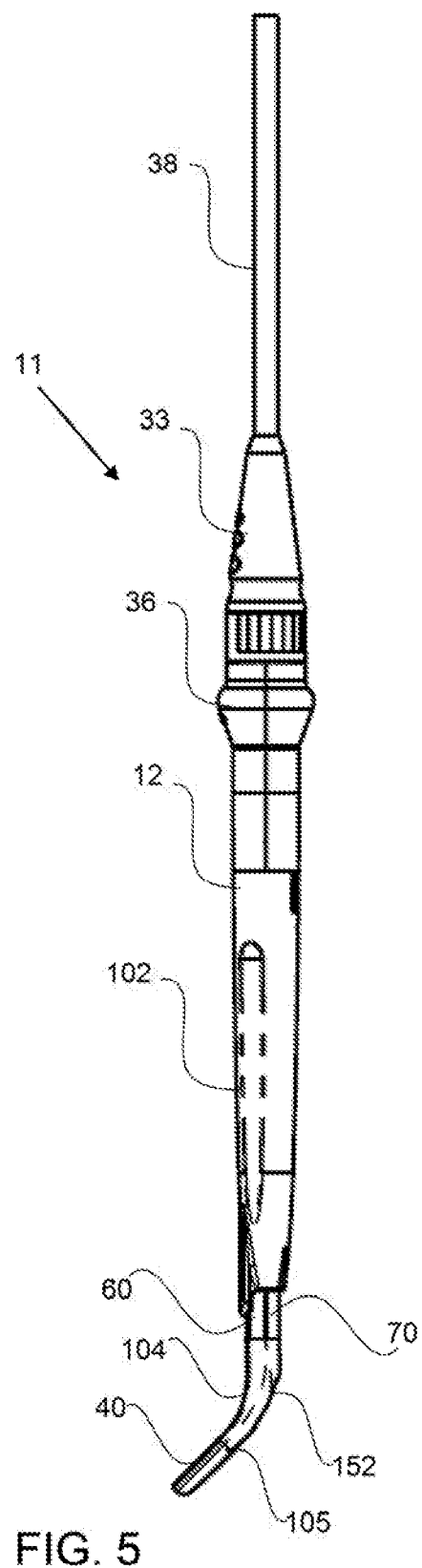

FIG. 5 shows a side view of the exemplary dental instrument shown in FIG. 2.

Figure 6:
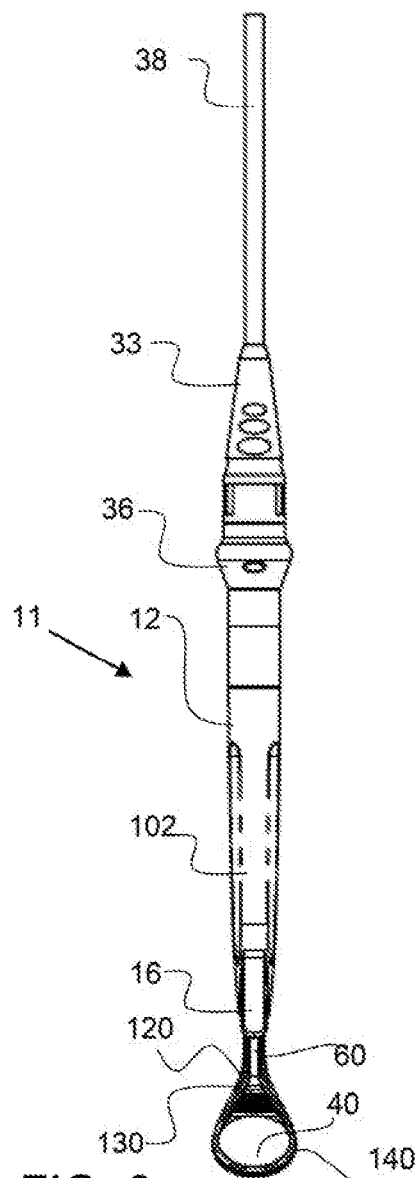

FIG. 6 shows a front view of the exemplary dental instrument shown in FIG. 2.

Figure 7:
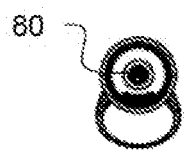

FIG. 7 shows a top view of the exemplary dental instrument shown in FIG. 6.

Figure 8:

FIG. 8 shows a bottom view of the exemplary dental instrument shown in FIG. 6.

Figure 9:
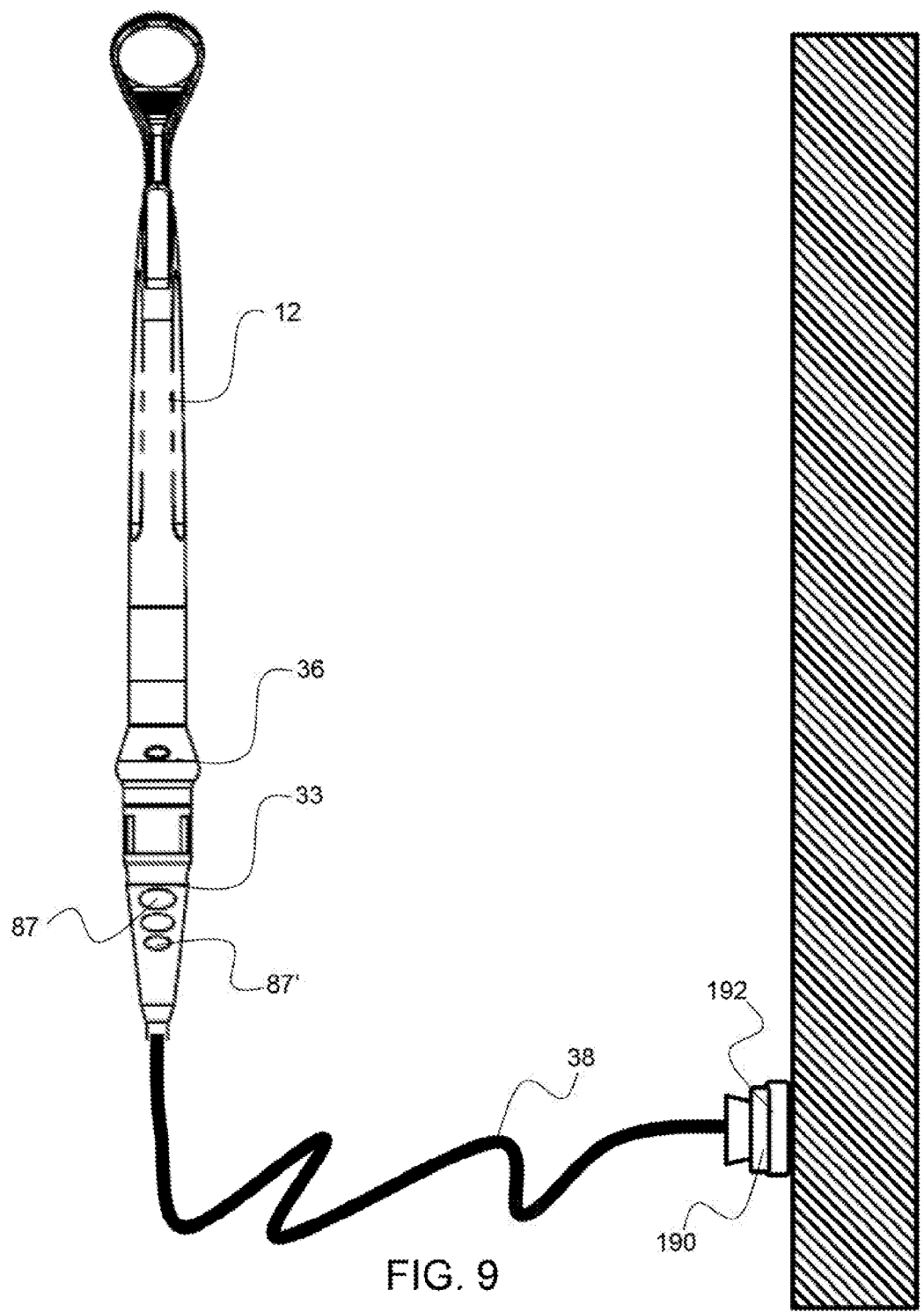

FIG. 9 shows an exemplary dental instrument coupled to a fixed source with a flexible connector attached to a fixed wall connector.

Figure 10:
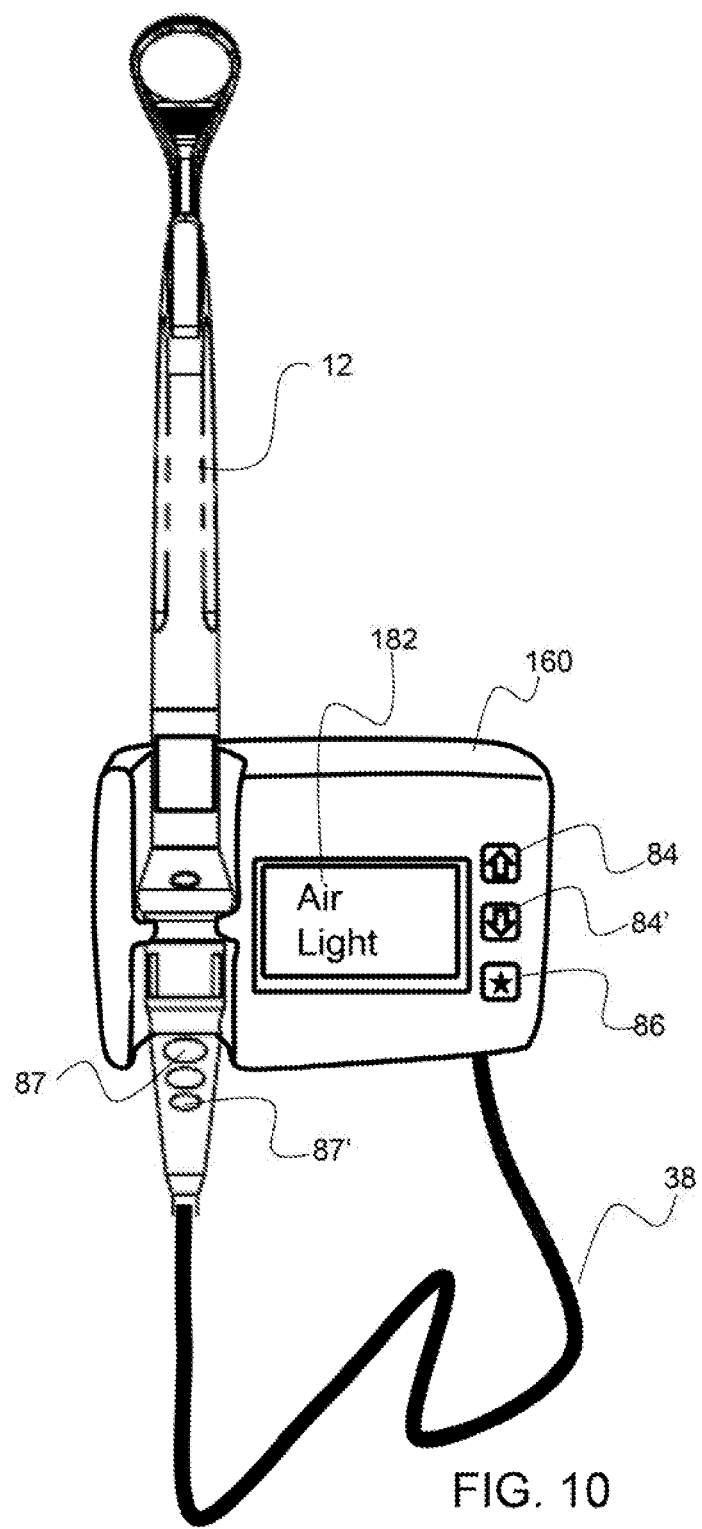

FIG. 10 shows an exemplary dental instrument configured in a docking station that has controls for the airflow level and the light source.

FIG. 11 shows a perspective front-side view of an exemplary optical component.

FIG. 12 shows a perspective back-side view of an exemplary optical component.

Figure 13:
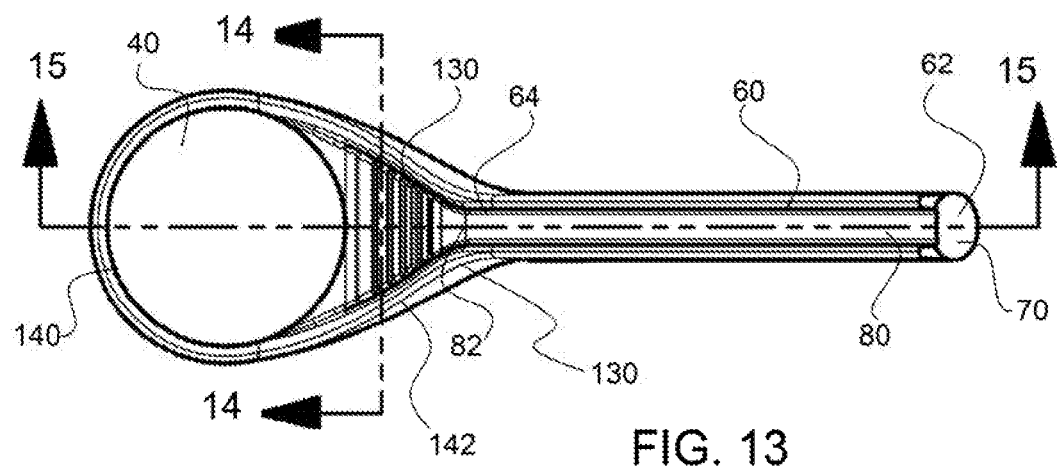

FIG. 13 shows a top view of an exemplary optical component.

Figure 14:
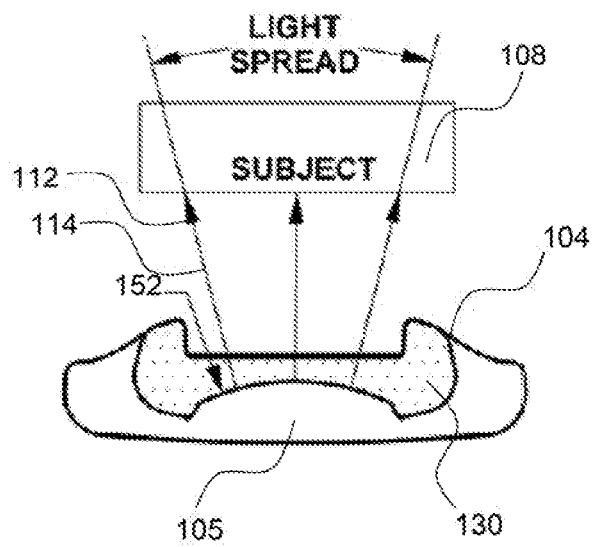

FIG. 14 shows a cross-section view of the land portion of the optical component along line 14-14 in FIG. 13.

FIG. 15 shows a cross-section view of he optical component along line 15-15 in FIG. 13.

FIG. 16 shows a cross-section view of the elongated member along line 16-16 in FIG. 15.

Figure 17:
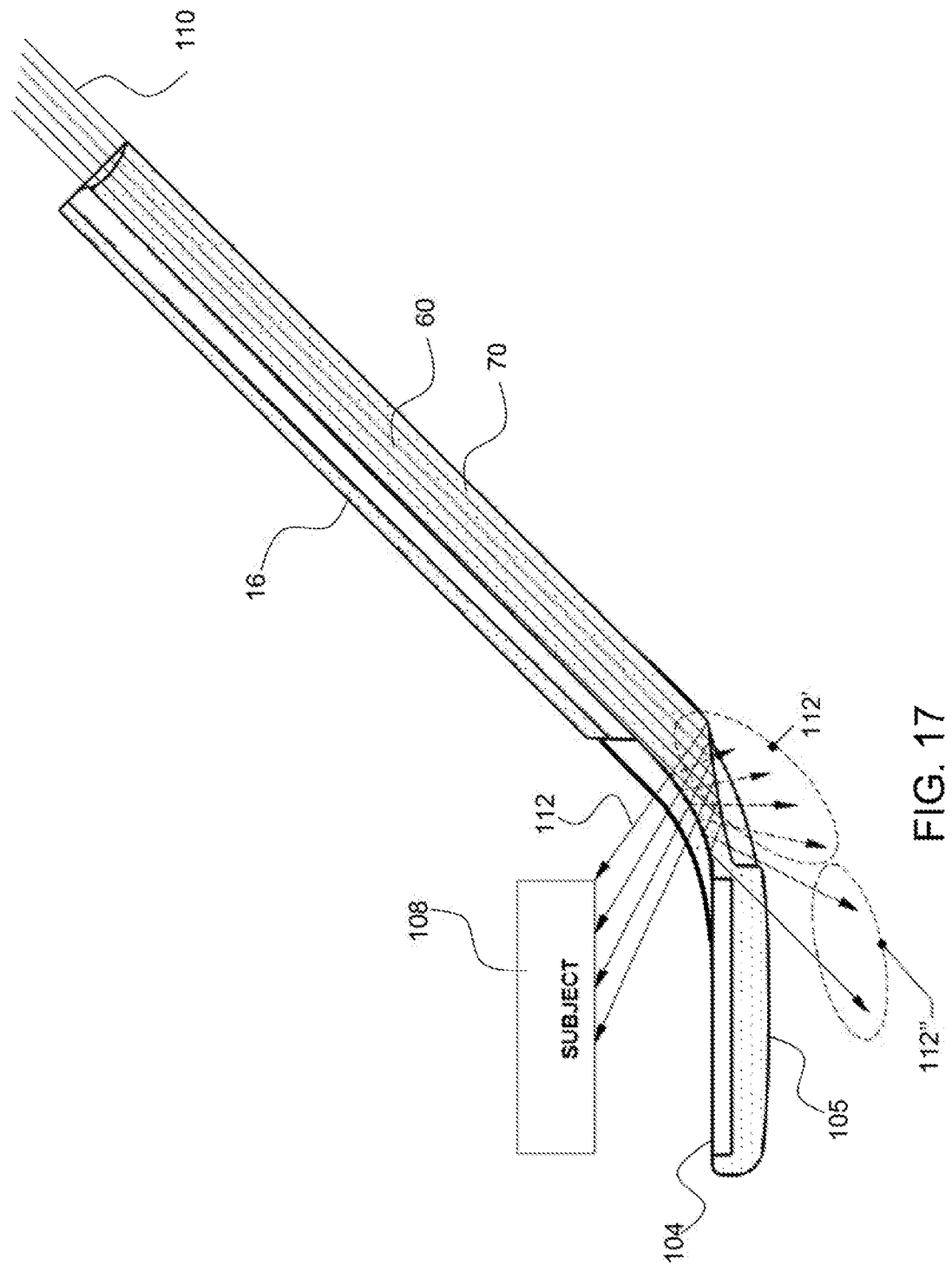

FIG. 17 shows a cross-section view of an elongated member that reflects light to the back-side of the optical component.

Figure 18:
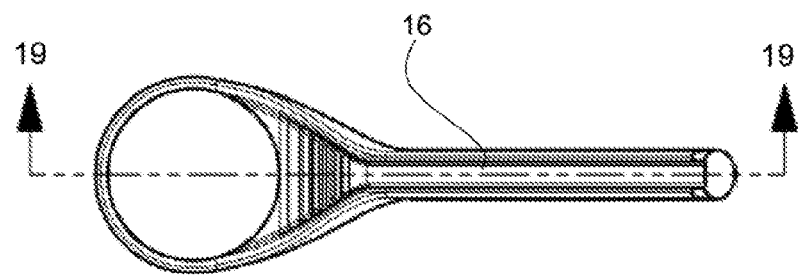

FIG. 18 shows a top view of an exemplary optical component.

Figure 19:
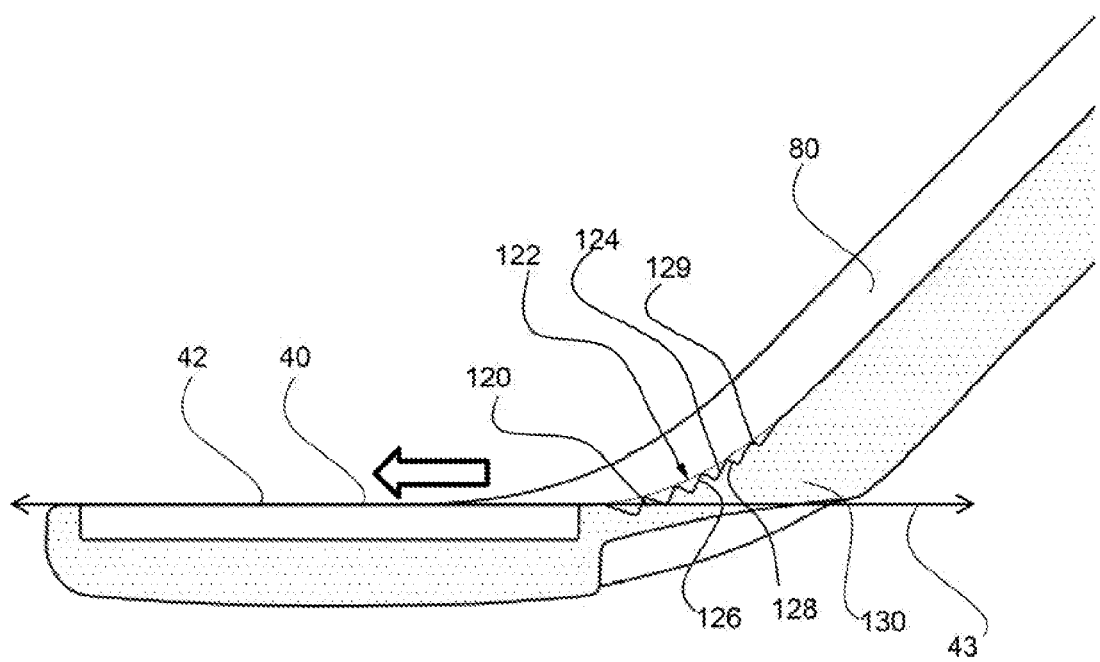

FIG. 19 shows a cross-section view of a portion of an exemplary elongated member along line 19-19 of FIG. 18.

Figures 20A, 20B:
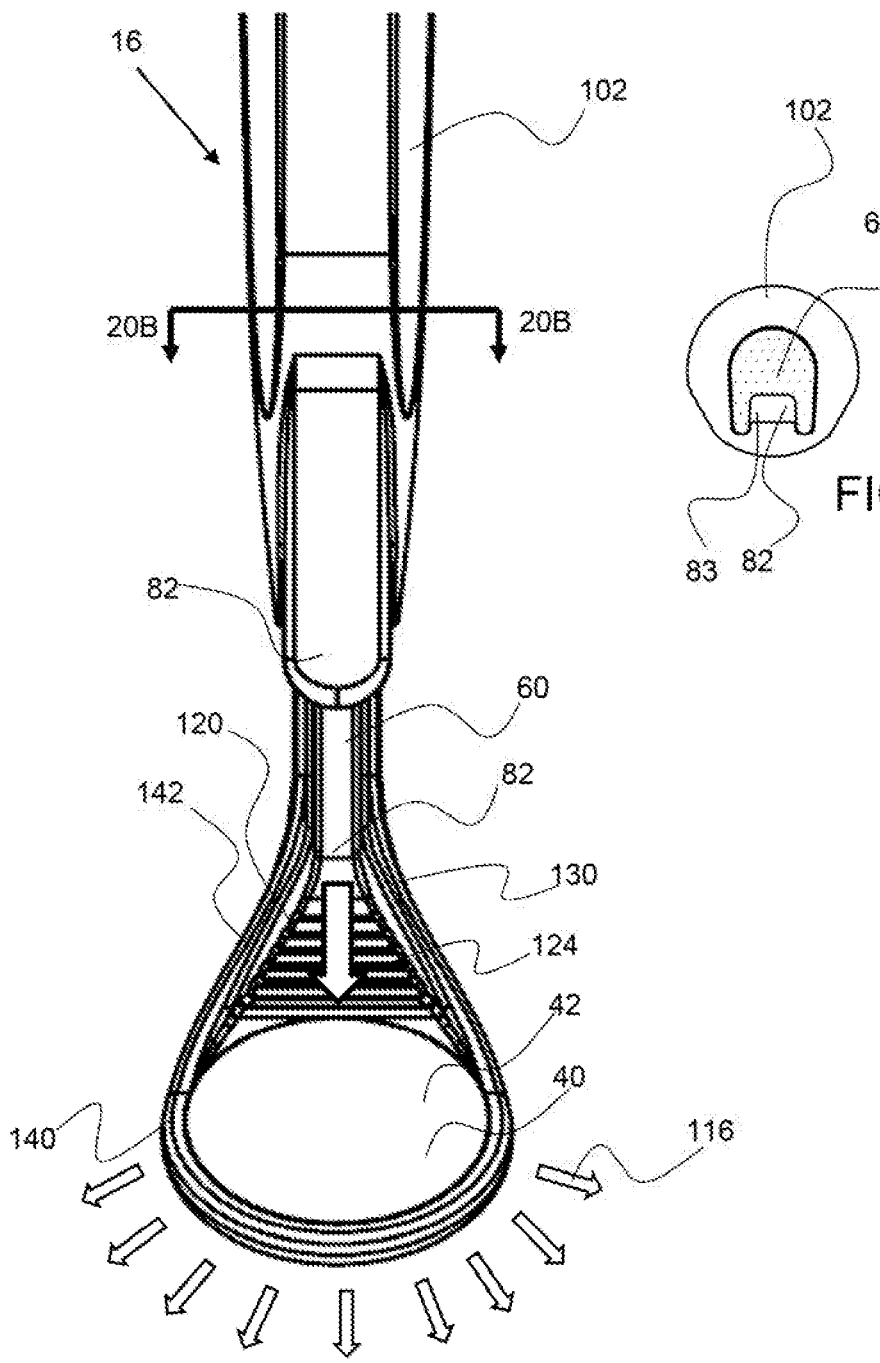

FIG. 20A shows a top-side view of an exemplary optical component having radiant light emitted from the mirror perimeter portion.

FIG. 20B shows a cross-section of the optical component along line 20B-20B of FIG. 20A.

Figure 21:
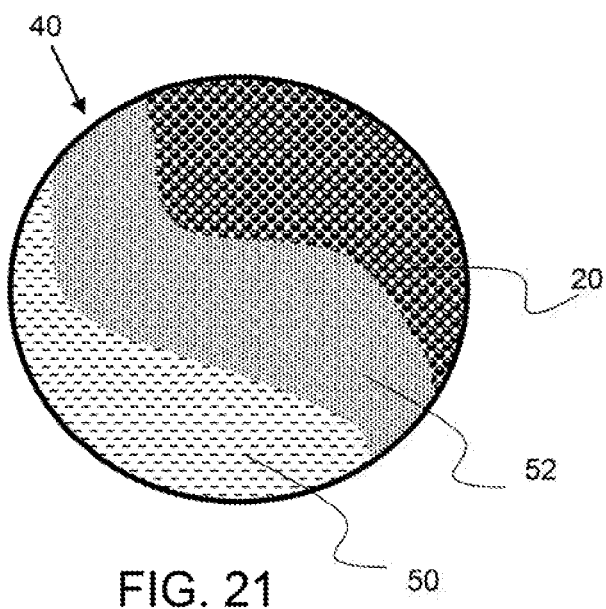

FIG. 21 shows a top-down view of an exemplary mirror having a plurality of layers.

Figure 22:
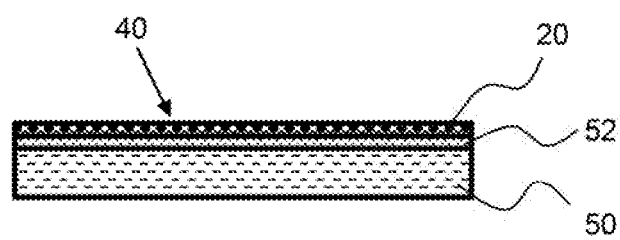

FIG. 22 shows a side view of n exemplary mirror having a plurality of layers.

Figure 23:
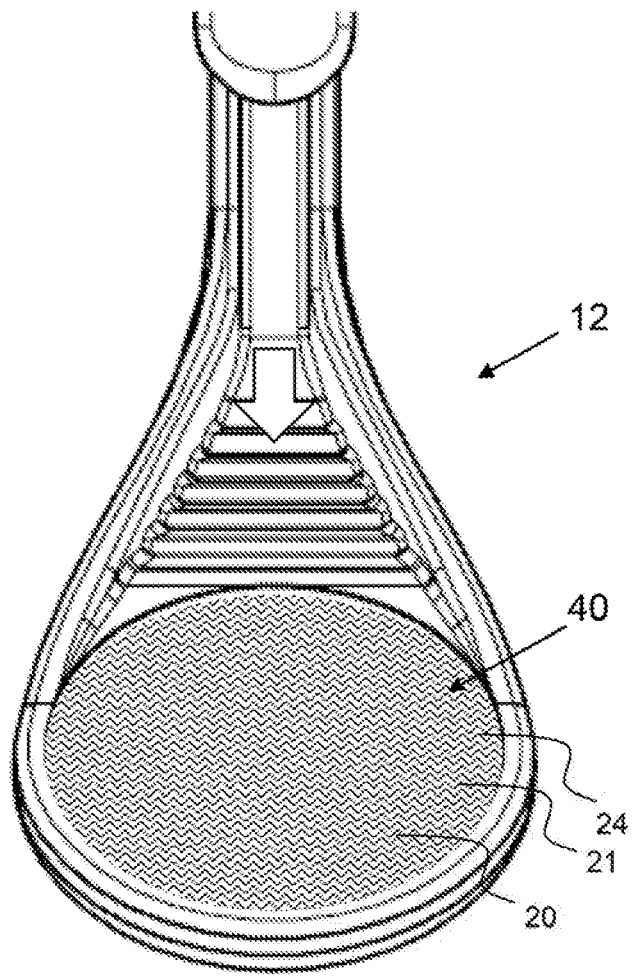

FIG. 23 show a perspective view of a dental mirror instrument having a mirror with a hydrophobic coating on the mirror surface.

Figure 24:
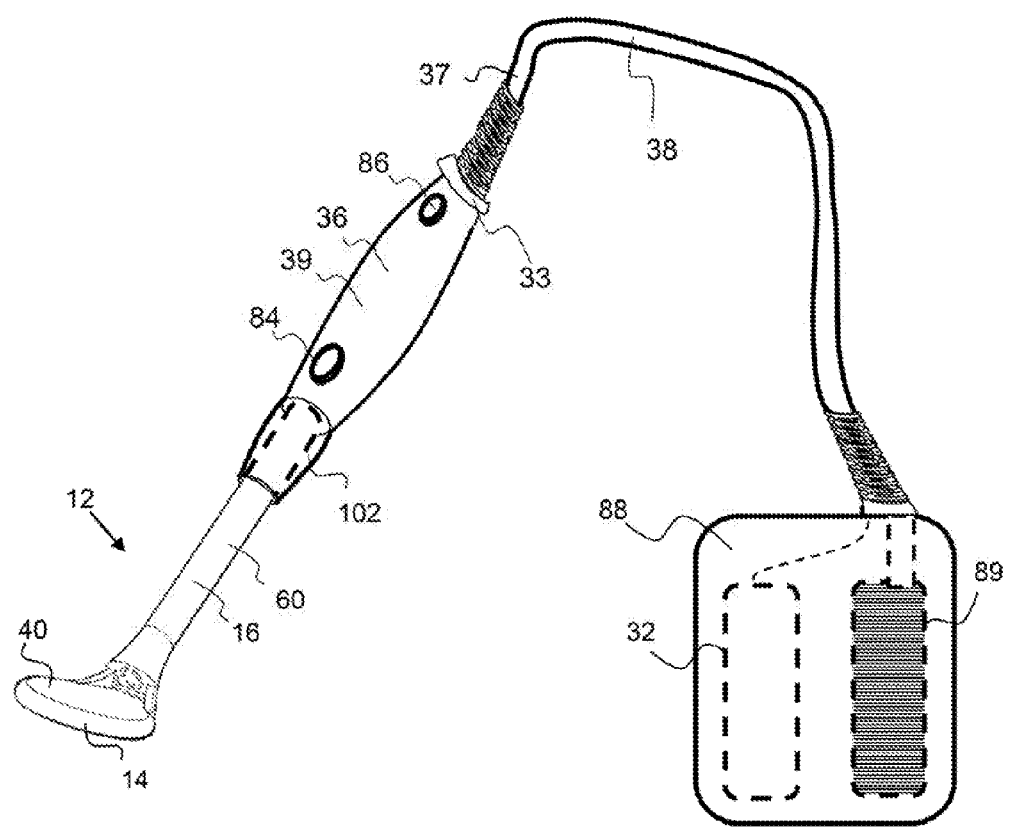

FIG. 24 shows a perspective view of an exemplary dental mirror instrument a having handle detachably attached with the connection end of an exemplary optical component and a flexible connector connecting an auxiliary pack with the handle.

Figure 25:
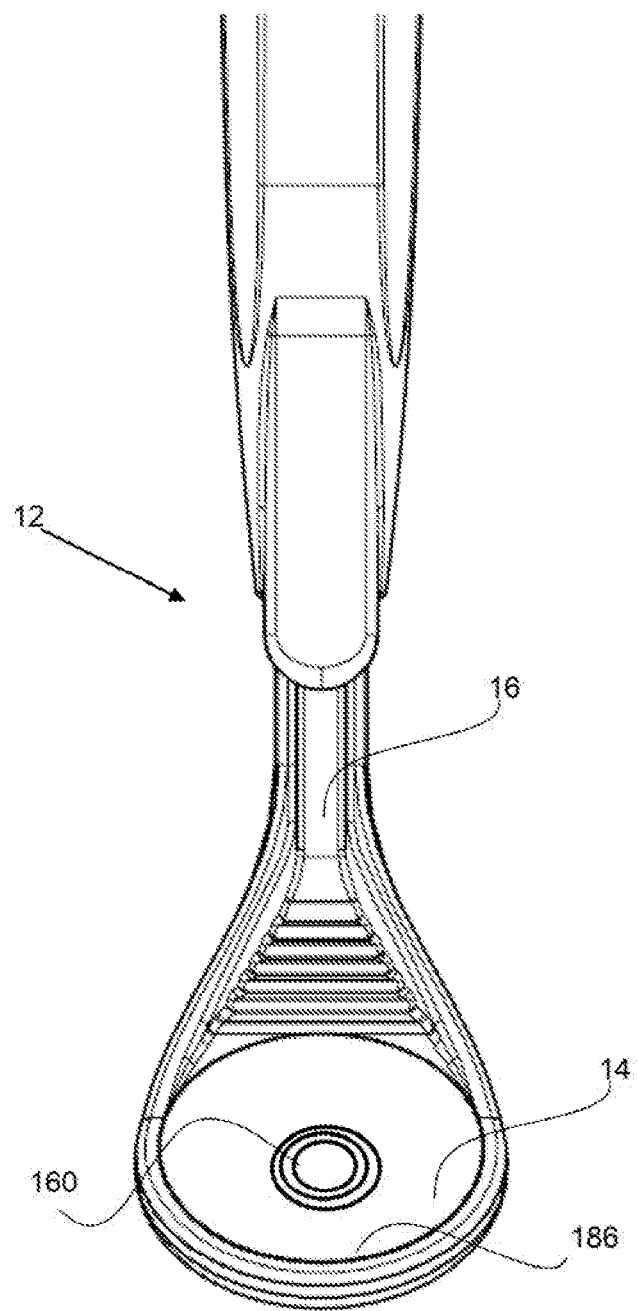

FIG. 25 shows a mirror portion having a camera.

Figure 26:
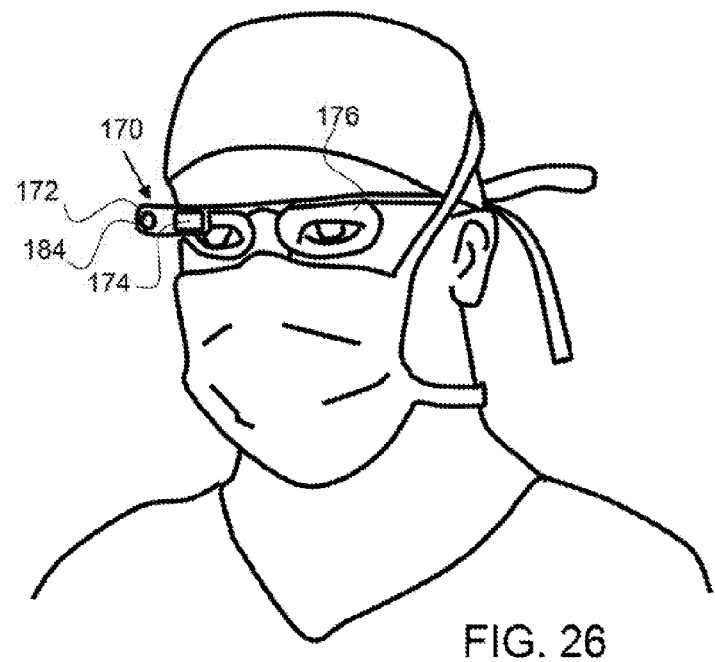

FIG. 26 shows a heads-up device that is coupled with a camera configured on the dental mirror instrument.

Figure 27:
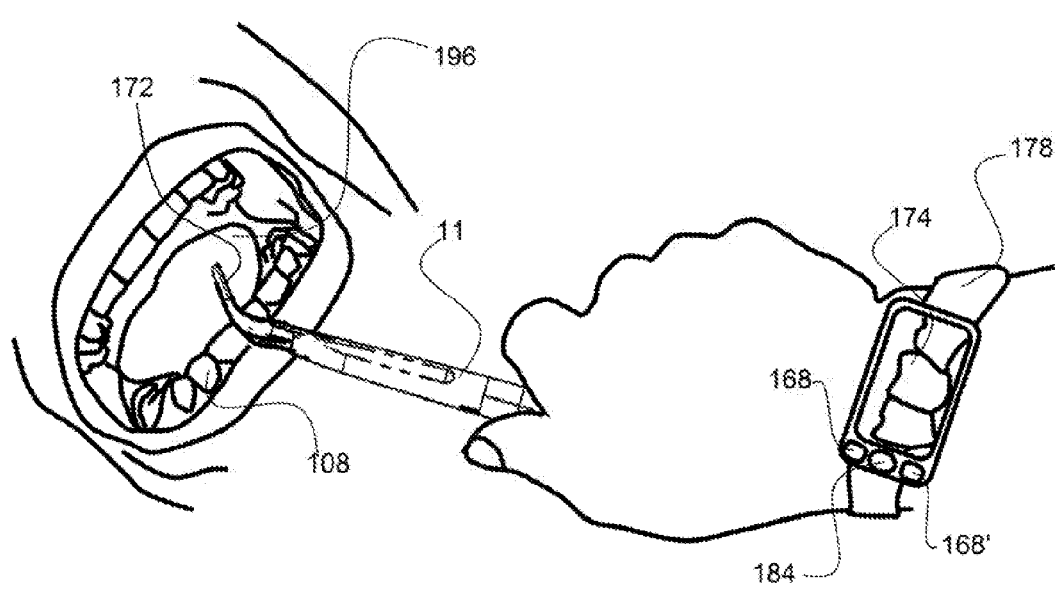

FIG. 27 shows a wrist display device that is coupled with the dental mirror instrument for showing a display of an oral cavity.

Figures 28, 29:
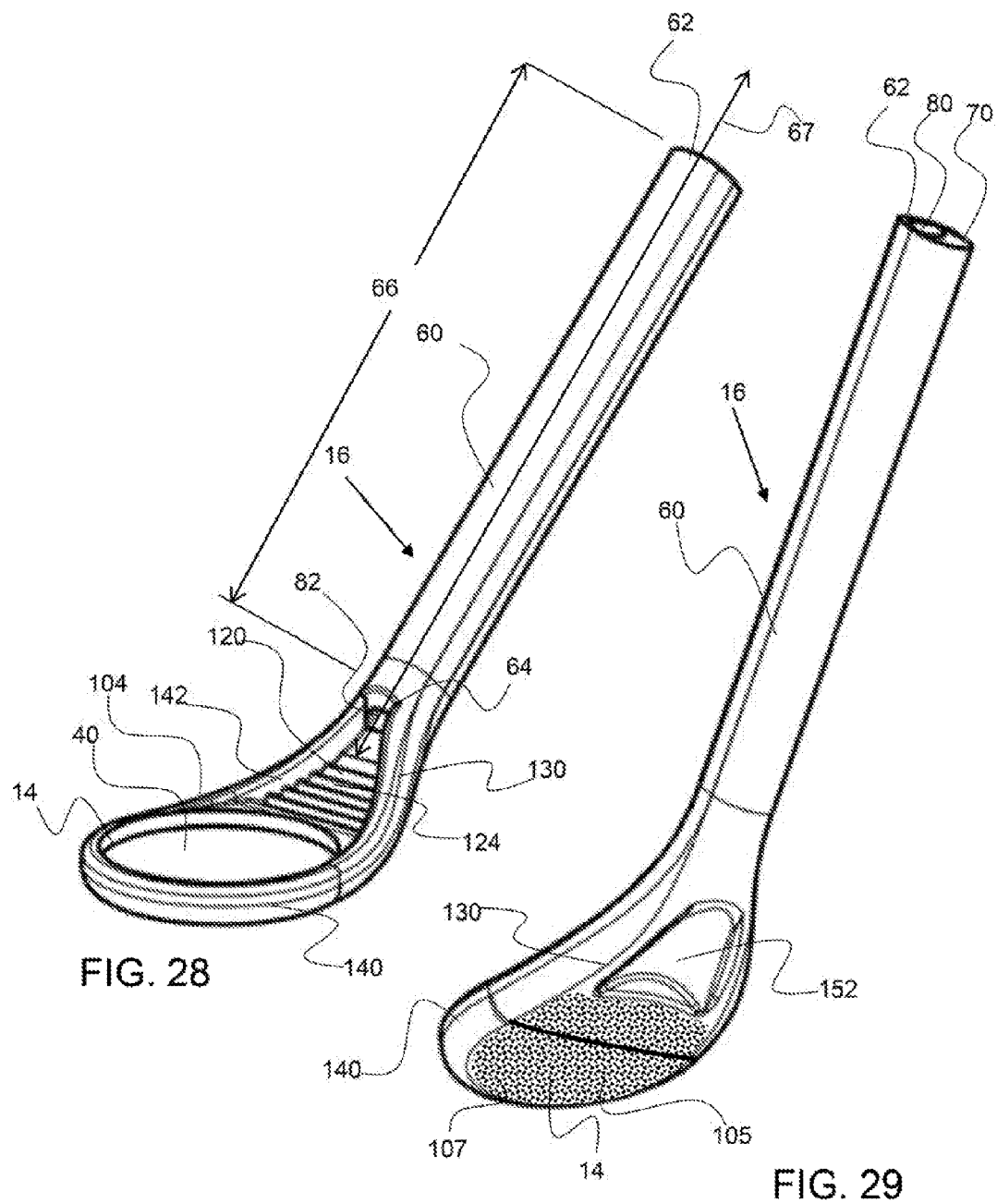

FIG. 28 shows a perspective front-side view of an exemplary optical component.

FIG. 29 shows a perspective back-side view of an exemplary optical component.

Figure 30:
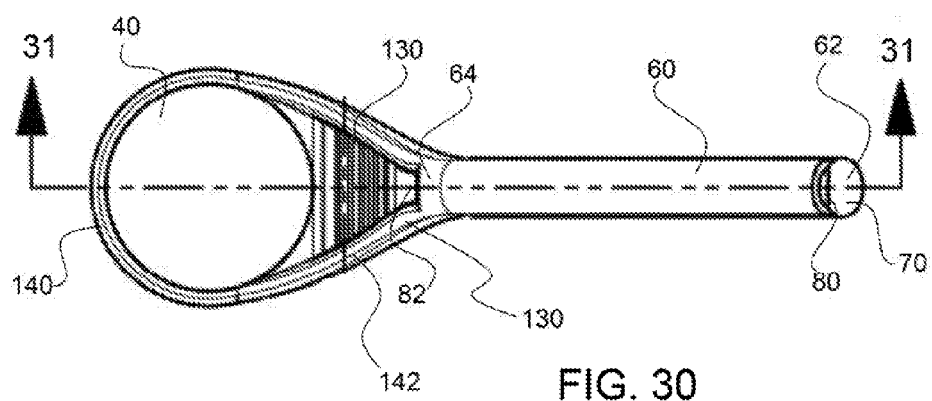

FIG. 30 shows a top view of an exemplary optical component.

FIG. 31 shows a cross-section view of the optical component along line 31-31 of FIG. 30

FIG. 32 shows a cross-section view of the elongated member along line 32-32 of FIG. 31.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated and/or magnified to show details of particular components. Therefore, specific structural and functional details disclosed herein are not to be interpreted as limiting, but merely as a representative basis for teaching one skilled in the art to variously employ the present invention.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein This is done merely for convenience, and to give a general sense of the scope of the invention. This description should be read to include one or at least one and the singular also includes the plural unless it is obvious that it is meant otherwise.

Certain exemplary embodiments of the present invention are described herein and illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

As shown in FIG. 1, an exemplary dental instrument comprises an optical component 16 having an elongated member 60, a land portion 130 and a mirror portion 14. The elongated member 60 has a light waveguide 70 and an airflow channel 83 that extend from the engagement end 62 to the mirror end 64. The optical sheath 102 is configured to slide down over the elongated member to produce an airflow conduit. The optical sheath has a length from the engagement end 62' to the terminal end 103. A Fresnel lens 120 in configured on the front-side of the land portion 130. The mirror 40 is configured within the mirror portion 14 and as described, may be detachable. The mirror portion 16 is configured to couple with the source component 36 to receive a flow of air and light from a light source. The source component is configured to couple with a source connector 33 to receive a flow of air and/or light or electric power for a light source configured in the source component. The source component may couple with a flexible connector.

As shown in FIG. 2 the components of the dental instrument 11 shown in FIG. 1 are attached. The optical sheath 102 is configured down over the elongated member to form the airflow conduit. The optical component 16 is attached to the source component 36 and the source component is attached to the source connector.

As shown in FIGS. 3 to 5, the dental mirror instrument 12 comprises an internal convex mirror surface 152 that reflects light from the back-side 105 to the front-side 104 and onto a subject, such as a tooth. The light waveguide 70 extends along the backside of the elongated member 60. Again, the optical component is attached to the source component 36.

As shown in FIG. 6, the optical component 16 comprises a Fresnel lens 120 in the land portion 130. The Fresnel lens is configured with a plurality of ridges that provide perpendicular surfaces for reflected light to be emitted from the front-side of the optical component 16.

As shown in FIG. 7 an airflow conduit extends down through the optical component.

FIG. 8 shows the back-side 105 of the mirror portion.

As shown in FIG. 9, a dental mirror instrument 12 is coupled to a fixed source 190, a wall connector 192. A fixed source may provide a flow of air and/or electrical power for a light source configured in the source component 36. A plurality of controls 87, 87', such as buttons or levers, may be used to turn on and/or off the flow of air or light, and/or increase or decrease the flow of air and/or the intensity or level of the light.

As shown in FIG. 10, an exemplary dental instrument 12 is configured in a docking station 160 having controls for adjusting the airflow level and/or the light source. A display shows that the air and light are on and airflow controls 84, 84 are configured on the docking station to increase or decrease the flow of air, respectively. A. light switch 86 enables the light to be activated. A flexible connector 38 couples the dental mirror instrument to the docking station 160. The docking station may have batteries to provide electrical power to the light source through the flexible connector, and/or a pump to provide a flow of air through the flexible connector to the dental mirror instrument. In another embodiment, the docking station is coupled with a source for the supply of power, such as an electrical outlet, or an airflow source.

As shown in FIG. 11, an exemplary optical component 16 comprises an elongated member 60 having a length 66 from an engagement end 62 to a mirror end 64 where it couples with the land portion 130. A Fresnel lens 120 is configured in the land portion and comprises a plurality of ridges 124 that extend perpendicularly to the length axis 67 of the elongated member 60. A pair of ribs 142 extend from the elongated member along either side of the Fresnel lens to the mirror portion 14 and guide an airflow from the airflow conduit to the mirror 40. The optical component 16 shown in a one-piece unit that may be injection molded out of single material and from a single cavity. An airflow channel 83 enables quick and easy injection molding of the part. A mirror perimeter portion 140 extends around the mirror 40 and in an exemplary embodiment emits radiant light.

As shown in FIG. 12, exemplary optical component 16 comprises a internally convex mirror surface 152 in the land portion 130 that is configured to reflect light towards the front-side and through the Fresnel lens. The back-side 105 of the mirror portion 14 comprises a modified surface 107, such as a frosted, reflective or opaque surface to reduce light emittance from the surface. A modified surface may block and/or reflect internal light from exiting the surface and in some cases reflect any internal light back into the material. The mirror perimeter portion 140 does not comprise a modified surface and may emit a radiant light.

As shown in FIG. 3, an exemplary optical component 16 comprises an engagement end 62 that is configured to receive light from a source component (not shown). The engagement end 62 may be concave in shape, at least in the light waveguide 70 portion. The elongated member 60 also comprises an airflow channel 83 extending along the length of the elongated member.

As shown in FIG. 14, the land portion 130 of the optical component comprises an internally convex mirror surface 152 that is configured to reflect light to the front-side 104 of the optical component. The reflected light rays 112 are spread out by the curvature of the internally convex mirror surface 152 to produce a task light 114 and, in use, are incident on a subject 108, such as a tooth. The internally convex mirror surface is concave in shape as seen from the outside of the optical component but is internally convex in shape. The light spread shown in FIG. 14 is in a direction substantially perpendicular to the length axis of the elongated member or optical component.

As shown in 15, an optical component 16 comprises a Fresnel lens 120 configured on the front-side 104 of the land portion 130. Light rays 110 are transmitted down along the elongated member 60 and through the light waveguide 70 where they reflect off the internally convex mirror surface 152 and through the Fresnel lens 120. The Fresnel lens comprises a plurality of ridges 124 made up of a rise 126 and a step 128. The rise is configured to provide a light emittance surface that is substantially perpendicular to the reflected light rays 112. Having a surface that is perpendicular to the light rays ensures that the light will be emitted from the surface and reduces reflection back into the surface. The step extends from the top of a first rise to the bottom of a subsequent rise and may be substantially perpendicular to the rise surface and substantially parallel with the reflected light. As shown, the internally convex mirror surface 152 produces a task light 114 that is spread out radially between the mirror portion and the elongated member or radially from the length axis of the elongated member, In an exemplary embodiment, the angle 156 between the light waveguide and the internally convex is maintained below 45 degrees resulting in total internal reflection of the light.

As shown in FIG. 16, an elongated member 60 comprises a light waveguide 70 and an airflow channel 83. The airflow channel 83 becomes an airflow conduit 80 when an optical sheath (not shown) is configured thereover. The channel having an open top-side enables the optical component to be injection molded easily and quickly as no rod is required to be insert molded around for the conduit.

As shown in FIG. 17, an optical component 16 that is not configured with a Fresnel lens will produce reflected light that exits the back-side of the optical component. The reflected light rays 112' are reflected from the smooth contoured surface on the front-side 104 of the land portion toward the back-side and are emitted out of the back-side. This reduces the intensity of the reflected light rays 11 that are emitted from the front-side of the optical component.

FIG. 18 shows a top view of an exemplary optical component 16.

FIG. 19 shows a cross-section view of a portion of an exemplary elongated member along line 19-19 of FIG. 18. The Fresnel lens 120 is configured with a plurality of ridges 124 having a rise 126 and a step 128 surface. In an exemplary embodiment, the plurality of ridge peaks 129 are configured in an airflow contour 122 that is concave along the length of the land portion 130, between the elongated member and the mirror portion, and are configured to direct the flow of air from the airflow conduit 80 across the mirror surface 42. The mirror 40 has a mirror plane axis 43 and water, fluids and debris may be more effectively removed when the flow of air is tangential with the mirror surface 42, as depicted by the bold arrow.

As shown in FIG. 20A, an exemplary optical component 16 has radiant light 116 emitted from the mirror perimeter portion 140. Light rays may be transmitted around the Fresnel lens 120 through the ribs 142 and into the mirror perimeter portion 140. The radiant light may provide general light of an oral cavity whereas the task light provides specific directed light to a subject or task area, such as a tooth. The ribs 142 extend up from either side of the Fresnel lens and act as baffles to guide the airflow from the airflow aperture 82 down over the mirror surface 42.

As shown in FIG. 20B, the optical sheath 102 extends around the elongated member 60 and to form an airflow conduit 83 by covering the airflow channel 82.

Referring now to FIGS. 21 to 23, an exemplary mirror 40 has a plurality of layers including a support base 50, a mirror coating 52 and a hydrophobic release surface 20. The hydrophobic release surface may be a coating 21 on the mirror.

As shown in FIG. 24, an exemplary dental mirror instrument 12 is detachably attached by a flexible connector 38 to an auxiliary pack 88. The auxiliary pack contains a battery 32 and a mini-pump 89. A user of the dental mirror instrument may connect the auxiliary pack with the handle by a source connector 33 and turn on the auxiliary pack to initiate the supply of power to the light configured within the handle or source component 36 and the supply of airflow from the mini-pump. The airflow produced by the mini-pump flows through the flexible connector, through a conduit in the handle, through the airflow conduit in the optical component and onto the mirror surface. An auxiliary pack may be placed in a user's pocket, attached to their belt, an examination table and the like. A light switch 86 or control, as well as an airflow control or switch may be configured on the dental instrument to enable a user to turn the light or airflow off and/or adjust a level.

As shown in FIG. 25, an exemplary optical component 16 is configured with a camera 160 in the mirror portion 14. The camera may have leads that extend up the elongated member to a transmitter, such as a short range transmitter, Bluetooth for example, for providing images to a display screen. The camera may be configured under a translucent or transparent cover 186 that protects the camera from exposure to fluids and also provides a flat planar surface and mirror plane for the flow of air to remove debris and fluid the mirror portion.

As shown in FIG. 26, a clinician is wearing eyewear 176 that has a heads-up device 170 having a display 174 coupled with a camera 172. Note that the display may be coupled with a camera that is in a mirror portion of a dental mirror instrument, as shown in FIG. 25, for example. As described herein, a user may manipulate the dental instrument having a camera to display a portion of an oral cavity. The heads-up display may receive verbal commands from the user to zoom, focus or adjust the position of the field of view of the camera for capturing a desired image. In addition, a heads-up display may be configured to record dictation throughout the use of a dental instrument for future review, documentation and use. A microphone 184 may also be configured on the heads-up device 170 for control of the magnification of the image being displayed. The magnification of the image may also be controlled by eye movement, wherein a sensor within the heads-up display monitors the eye and changes magnification level as a function of eye position.

As shown in FIG. 27, a dental mirror instrument 11 is configured within an oral cavity 196 and a camera 172, configured in the mirror portion of the dental instrument, is capturing images of the oral cavity and providing them to a wrist display device 178 having a display 174. As shown, a plurality of teeth are being displayed on wrist display device and the magnification of this displayed image may be manipulated by voice, or manual controls on the writ display device. For example, a microphone 184, configured on the wrist display device, enables a user to change the magnification of the displayed image. A user may verbally request that the image be enlarged or reduced in magnification as desired. The microphone may be coupled with a controller that zooms the camera in or out on an object to be displayed. In another embodiment, the magnification and reduction of the displayed image is a digital magnification and/or reduction of the digital image. Magnification controllers 168, 168' may be configured on the wrist display device for controlling the magnification level of the image being displayed. The magnification controller may be a manually manipulated control interface including, but not limited to, a single lever or button or a plurality of buttons, levers, toggles switches or levers and the like.

Referring now to FIGS. 28 and 29, an exemplary optical component 16 comprises an elongated member 60 having an airflow conduit 80. The airflow conduit 80 and light waveguide 70 are shown be adjacent each other at the engagement end 62 in FIG. 29. The optical component can be injection molded but would require a removable pin or post to form the airflow conduit in the part.

As shown in FIGS. 30 to 31, an exemplary optical component 16 comprises an engagement end 62 that is configured to receive light from a source component. The engagement end 62 comprises an airflow conduit 80. An airflow aperture 82 is configured at the mirror end 64 of the elongated member. FIG. 32 shows the cross-section of the elongated member 80 and the airflow conduit 80 adjacent the light waveguide 70.

It will be apparent to those skilled in the art that various modifications, combinations and variations can be made in the present invention without departing from the spirit or scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. A dental instrument comprising:
   a) an optical component comprising;
      i) a mirror portion comprising;

a mirror;
a mirror surface;
a mirror plane axis;
ii) an elongated member having a length and a length axis from an engagement end to a mirror end;
iii) a light waveguide extending along the length of the elongated member having an engagement end for receiving light from a light source and configured to transmit said light along the light waveguide to a land portion;
iv) an airflow conduit extending along the length of the elongated member having an airflow aperture configured at the mirror end for dispensing a flow of air over the mirror surface;
v) said land portion configured between the elongated member and the mirror portion having a front-side and a back-side, and comprising:
a Fresnel lens positioned on the front-side of said land portion comprising a plurality of ridges extending across the land portion in a substantially perpendicular direction to the length axis of the elongated member;
wherein the Fresnel lens is configured to emit a reflected light from the back-side of the land portion from the optical component to produce a task light;
wherein the ridges comprise a step and a rise, wherein the rise is a planar surface that extends substantially perpendicularly to a reflected light from the back-side of the land portion; and
wherein the step is a planar surface that extends substantially parallel to a reflected light from the back-side of the land portion.

2. The dental instrument of claim 1, wherein the ridges are configured in a convex shape along the front-side of the land portion from the elongated member to the mirror portion.

3. The dental instrument of claim 1, wherein the land portion further comprises an internally convex shaped mirror surface configured along a portion of the back-side of the land portion to reflect light toward the front-side of the land portion and through the Fresnel lens;
wherein the ridges comprise a step and a rise, wherein the rise is a planar surface that extends substantially perpendicularly to a reflected light from the internally convex shaped mirror surface; and
wherein the step is a planar surface that extends substantially parallel to a reflected light from the internally convex shaped mirror surface.

4. The dental instrument of claim 1, further comprising a light emitting perimeter portion that extends radially around a portion of the mirror; wherein said light waveguide is integrally coupled with the light emitting perimeter portion;
wherein a portion of said light that is transferred along the light waveguide is transmitted to the light emitting perimeter portion where the light is emitted from the light emitting perimeter to provide a radiant light.

5. The dental instrument of claim 4, wherein the land portion further comprises a pair of ribs that extend around the Fresnel lens and couple the light waveguide with the light emitting perimeter to produce a radiant light that is projected from the light emitting perimeter.

6. The dental instrument of claim 1, further comprising an optical sheath configured over the elongated member portion of the optical component from the engagement end to a terminal end.

7. The dental instrument of claim 6, wherein the airflow conduit is an open channel and the optical sheath, configured over the elongated member, forms an enclosed airflow conduit.

8. The dental instrument of claim 6, wherein the optical sheath is detachably attachable to the optical component and is configured to slide over at least a portion of the elongated member.

9. The dental instrument of claim 1, wherein the mirror is detachably attachable to the optical component.

10. The dental instrument of claim 1, wherein the light waveguide consists of a plastic material having an index of refraction of 1.3 or more.

11. The dental instrument of claim 1, wherein the light waveguide is configured on a back-side of the elongated member and the airflow conduit is configured on a front-side of the elongated member.

12. The dental instrument of claim 1, wherein the light waveguide has an outer surface that forms an outer surface of the elongated member.

13. The dental instrument of claim 1, wherein the mirror portion, the elongated member and the land portion are a one-piece unit.

14. The dental instrument of claim 13, wherein the one-piece unit is made out of a of a plastic material having an index of refraction of 1.3 or more.

15. The dental instrument of claim 1, further comprising a frosting over a portion of the optical component.

16. The dental instrument of claim 1, wherein the light waveguide has a concave engagement end.

17. The dental instrument of claim 1, further comprising a hydrophobic release surface on the mirror surface.

18. The dental instrument of claim 1, wherein the hydrophobic release surface is an etched surface of the mirror surface.

19. The dental instrument of claim 1, further comprising:
a) a light source located adjacent the engagement end of the light waveguide;
b) an airflow source coupled with the engagement end of the optical component that provides the flow of air through the airflow conduit;
wherein the mirror portion of the dental instrument is illuminated and self-cleaning;
whereby said flow of air is directed across the mirror surface to keep the mirror surface clear of liquid, fog and debris.

20. The dental instrument of claim 1 wherein the light source is a light emitting diode.

21. The dental instrument of claim 19, wherein the light source is configured in a source component configured to detachably attach to the optical component.

22. The dental instrument of claim 19, further comprising a flexible connector that is coupled with the source component wherein the flexible connector is configured to couple with an electrical power supply for powering the light source.

23. The dental instrument of claim 19, further comprising a flexible connector that is coupled with the source component, wherein the flexible connector is configured to couple with an airflow supply to the airflow conduit of the optical component.

24. The dental instrument of claim 19, further comprising auxiliary pack having a battery that provides power to the light source and a pump for providing the flow of air to the airflow conduit of the optical component, wherein the dental instrument is portable and does not require a hard connection for the light source or the flow of air.

25. A dental instrument comprising:
a) an optical component comprising;
  i) a mirror portion comprising;
    a mirror;
    a mirror surface;
    a mirror plane axis;
    a light emitting perimeter portion that extends radially around a portion of the mirror;
  ii) an elongated member having a length and a length axis from an engagement end to a mirror end;
  iii) a light waveguide extending along the length of the elongated member having a source end for receiving light from a light source;
wherein said light waveguide is integrally coupled with the light emitting perimeter portion; wherein said light transferred along the light waveguide from the source end to the light emitting perimeter portion where a portion of said light is emitted from the light emitting perimeter to provide a peripheral light around the mirror portion;
  iv) an airflow conduit extending along the length of the elongated member having an airflow aperture configured at the mirror end for dispensing a flow of air over the mirror surface;
  v) a land portion configured between the elongated member and the mirror portion having a front-side and a back-side, and comprising:
    a Fresnel lens positioned on the front-side of said land portion and configured to disperse the light and comprising three of more ridges extending across the land portion on the front-side in a substantially perpendicular direction to the length axis of the elongated member; and
wherein the ridges are configured in a convex shape along the front-side of the land portion from the elongated member to the mirror portion;
an internally convex shaped mirror surface configured along a portion of the back-side of the land portion to reflect light toward the front-side of the land portion and through the Fresnel lens,
wherein the ridges comprise a step and a rise, wherein the rise is a planar surface that extends substantially perpendicularly to a reflected light from the internally convex mirror surface; and
wherein the step is a planar surface that extends substantially parallel with said reflected light from the internally convex mirror surface.

\* \* \* \* \*